United States Patent [19]

Williamson

[11] 4,181,009
[45] Jan. 1, 1980

[54] APPARATUS FOR COUNTING PARTICLE CONTAMINATION IN A LIQUID

[75] Inventor: William A. Williamson, Niles, Mich.
[73] Assignee: Clark Equipment Company, Buchanan, Mich.
[21] Appl. No.: 899,662
[22] Filed: Apr. 24, 1978
[51] Int. Cl.$^2$ ............................................. G01N 15/00
[52] U.S. Cl. ....................................................... 73/61.4
[58] Field of Search ............... 73/61 R, 432 PS, 61.4; 235/92 PC; 324/71 PC; 356/102

[56] References Cited
U.S. PATENT DOCUMENTS

| | | | |
|---|---|---|---|
| 3,321,977 | 5/1976 | Topham | 73/422 GC |
| 3,952,580 | 4/1976 | Bennett | 73/61.4 |

*Primary Examiner*—Gerald Goldberg
*Assistant Examiner*—Joseph W. Roskos
*Attorney, Agent, or Firm*—J. C. Wiessler

[57] ABSTRACT

Improved apparatus for counting particle contamination in a liquid which is adapted for either on-line or bottle sampling. It includes a hydraulic cylinder and piston arranged to be actuated to eject a measured volume of sample liquid through a particle counter and sensor device at a pressure which will drive liquid entrained air into solution or compress the same such that air bubbles will not be counted. The measured volume is effected by operating the particle counter device only during piston travel between predetermined locations in the cylinder with the cylinder liquid connected to a hydraulic system only through the counter device. Valving is provided for operator selection of on-line or bottle sampling. When no sample is being taken a portion of the liquid flowing in a main hydraulic system flows through conduit means which is a part of the sampling circuit in parallel with a portion of the main circuit, of which conduit means the cylinder forms a part.

18 Claims, 2 Drawing Figures

APPARATUS FOR COUNTING PARTICLE CONTAMINATION IN A LIQUID

BACKGROUND OF THE INVENTION

Control of contamination in liquids utilized in such things as industrial, vehicular and machine hydraulic systems is of importance, and often of critical importance, to the proper functioning of the system and components therein. Particulate contamination is of special concern, and particle counter devices have been employed for analyzing hydraulic fluid to determine the amount of particle contamination therein. Conventionally, particle counter sensors presently available are designed primarily for laboratory use utilizing a sampling method known as "bottle sampling", which is preferred in a laboratory setting because of the versatility available to deal with a large variety of fluids under different contamination conditions. However, it requires considerable expertise to operate the particle counter and to correctly interpret the results. Also, mishandling the sample while it is being taken or counted can add contaminant to the liquid, producing erroneous results.

My device provides an improved method of metering liquid through an automatic particle counter. In the on-line method of particle counting, referred to above, a continuous flow of liquid is passed through the sensing head of a particle counter which flow is regulated to a selected value and the particle count is done on a timed basis, assuming a constant flow rate. It has been found that this is not always reliable because in hydraulic oil in particular the viscosity is temperature dependent so that normal flow sensing devices are not accurate. For example if the oil is hot it will flow through certain flow controlled devices more rapidly than if it is cold. Therefore, more oil will pass through the sensor of the particle counter than a flow meter would indicate, thereby giving an erroneous reading.

Also encountered is the problem of inherent error resulting from entrained air bubbles in the sample or system liquid. The particle counter cannot discriminate between contaminants and entrained air bubbles and counts both, thereby giving erroneous readings. It has proven to be difficult to remove the same in on-line systems.

In the manufacturing environment, for example, on-line sampling is much preferred because the machine being checked is close to the particle counter so that the counter may be directly connected into the machine, the chance of contaminating the sample is essentially nil, the technical expertise required is less than with bottle sampling, and because both the liquid and allowable contaminant level are known, particle counting becomes a verifying procedure. Air bubbles in hydraulic oil are "seen" by the counter as particles and are therefore counted, which results in an erroneously high particle count and frequently leads to needless rejection of the machine. Also, inability to control the flow rate precisely through the particle counter has been a problem heretofore.

U.S. Pat. No. 3,952,580, granted Apr. 27, 1976, represents the closest known prior art in which relatively primitive apparatus is provided to attempt to solve such problems as above mentioned.

It is a primary object of this invention to provide improved apparatus for accurate counting of particle contamination in a liquid, whether the apparatus is utilized for on-line or bottle sampling.

Other objects and advantages will become apparent from the following description taken in conjunction with the accompanying drawings.

DETAILED DESCRIPTION

Figure 1:
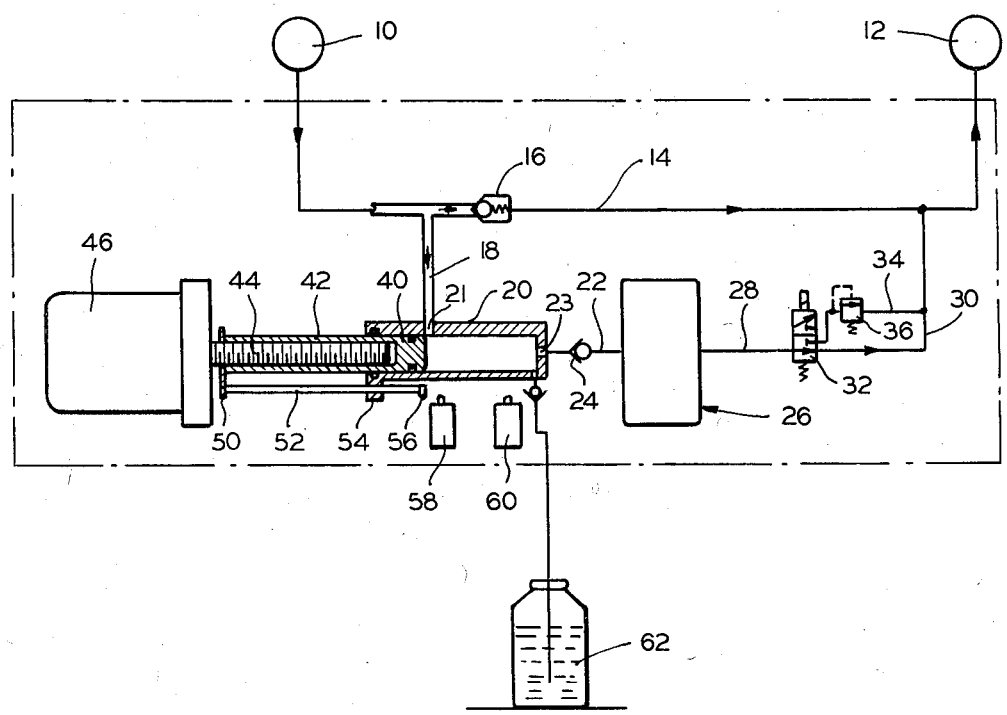
FIG. 1 is a schematic view of one embodiment of my invention.

Referring to FIG. 1, the hydraulic oil to be sampled is represented as flowing from a source 10 to a location 12 by way of a conduit 14 in which is located a check valve 16 which provides back pressure and permits hydraulic oil to flow through a conduit 18 into a cylinder 20. The liquid then flows through conduit 22 having therein a check valve 24 and through the sensor of a particle counter represented diagrammatically at 26, from whence it flows back into conduit 14 by way of either conduits 28, 30 and one side of a double acting solenoid operated valve 32, or by way of conduits 28, 34 and 30 and the opposite side of valve 32 and a high pressure relief valve 36. Particle counter and sensor unit 26 may be Model No. 345 manufactured by Royco Instruments, Inc. of Menlo Park, Calif. It is important to note that the flow through on-line conduit means which parallels conduit 14 of the main hydraulic system includes cylinder 20 and spaced ports 21 and 23 thereof as a part of said conduit means. Further discussion concerning the cylinder 20 as being a part of the said conduit means, which includes conduits 18, 22, 28, 30 and 34, will appear below.

A piston 40 is located in cylinder 20 shown in retracted position. It has an elongated cup-shaped portion 42 which is internally threaded and which extends outwardly of the cylinder for connection with a rotatable screw 44 adapted to be operated by a low horsepower constant speed gear motor 46. As the gear motor is rotated the rotational movement is converted to linear movement at piston 40.

At the one end of piston 40 is secured a lug 50 to which is fixed a rod 52 which passes through an opening in a lug 54 on the one end of cylinder 20. A probe 56 is connected to the end of rod 52. Lug 54 and stem 52 prohibit rotational movement of piston 40 during linear movement thereof in cylinder 20. Probe 56 is adapted to operate switch assemblies 58 and 60 during forward movement of the piston which starts and stops the counter 26.

In normal operation part of the oil traveling from source 10 to point 12 is forced by check valve 16 to pass through the on-line by-pass sampling circuit in a continuous flow of oil. When the operator of the machine or other apparatus to the hydraulic system of which my invention is connected desires to take a sample, gear motor 44, 46 is energized which starts piston 40 moving forwardly in cylinder 20. The initial portion of piston movement seals conduit 18 from the cylinder so that no additional oil can enter the sampling circuit, at which time there is a fixed volume of oil trapped within the sampling circuit. The control of the gear motor is connected such that solenoid valve 32 is actuated when the motor is energized to connect conduits 28 and 30 by way of pressure relief valve 36 and line 34.

Continued movement of piston 40 causes probe 56 to trip switch 58 which starts the operation of particle counter 26 which continues until the piston moves to such a position that probe 56 trips switch 60 stopping counter 26. It will be appreciated by persons skilled in the art that additional switches can be incorporated to de-energize the gear motor, reset the counter, reverse the motor in order to return piston 40 to its illustrated position, and to de-energize solenoid valve 32 to return it to its illustrated position.

As will now be apparent, the rate of flow through counter 26 can be precisely controlled by a selected combination of motor speed and piston size, a fixed volume being always delivered to the counter during the contamination count irrespective of oil viscosity as controlled by the selected positions of control switches 58 and 60. With oil under relatively high pressure, preferably about 1500 psi as controlled by valve 36, it will be seen that air bubbles entrained in the oil are either driven into solution or compressed to such a small size that they will not be counted by the particle counter.

To take a particle count the operator need only hook up two quick disconnects, not shown, between the sampler circuit conduits 18, 30 and the main system conduit 14, start the prime mover, pump or other source pressure apparatus in the hydraulic system being sampled, and start gear motor 46. The remainder of the operation is automatic with the sampler device starting and stopping counter 26 at the correct times; the device is reset by running motor 46 in reverse following each sampling operation. A container 62 is illustrated to provide a source of oil fill for the cylinder during retraction of the piston preparatory to taking the next sample. As illustrated, container 62 should be filled with oil following a predetermined number of sample takings, such as by connection to the sump of the main system, not shown. Also, if it is desired to test a particular liquid sample in a not on-line test it may be done by utilizing container 62 for a selected liquid sample while disconnecting conduits 18 and 30 from the main circuit, plugging port 21, and reconnecting line 30 to container 62, for example. It should be noted that on-line sampling will provide more accurate sampling results relative to a hydraulic system than bottle samples, for example, because the hydraulic system fluid is continuously flowing through the by-pass sampling circuit and can be tested at any time under any actual operating conditions.

Figure 2:
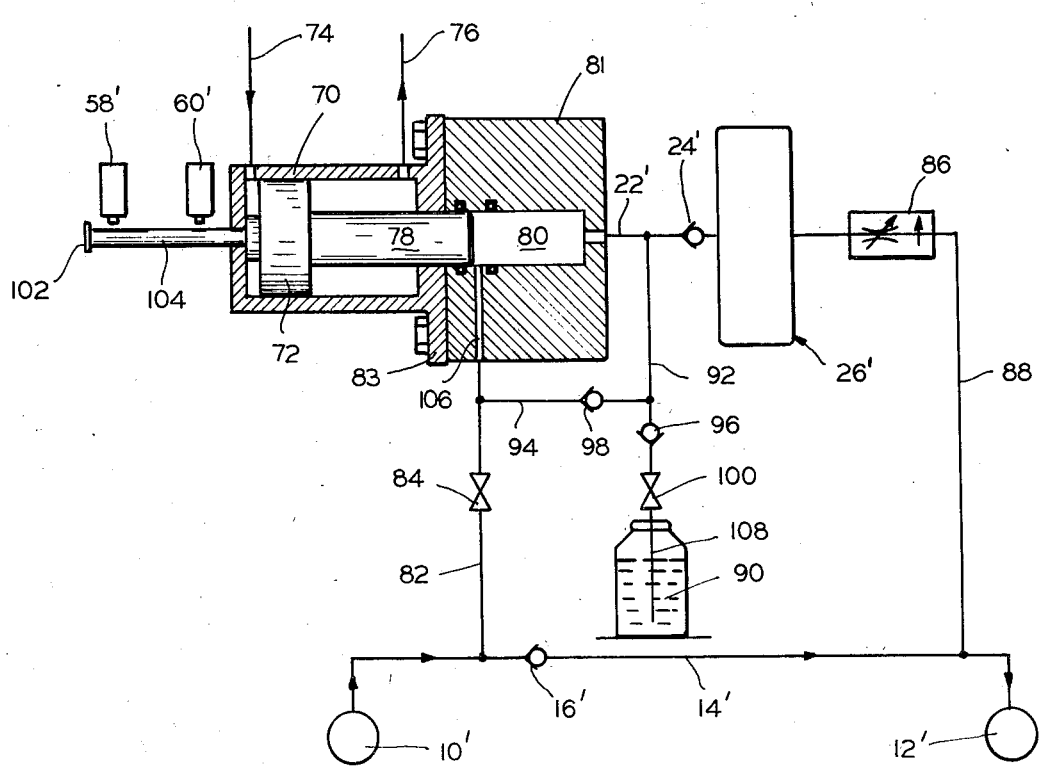
FIG. 2 is a schematic view of a second and preferred embodiment of the invention.

In my preferred embodiment as shown in FIG. 2 similar elements have been similarly numbered but carry a prime designation. An air cylinder and piston 70, 72 replaces the gear motor and screw arrangement of FIG. 1, the piston being driven in a forward direction by air pressure supplied by conduit 74 and in a reverse direction by air pressure supplied by conduit 76. A connected hydraulic piston 78 is operable in a cylinder 80 which is formed in a housing 81 and a bolted on cover 83 of cylinder 70, the by-pass sampling circuit comprising conduit 82 having a manual valve 84 entering one end of cylinder 80, and conduit 22' connected from the remote end of the cylinder to conduit 14' by way of check valve 24', counter 26' and a pressure compensated flow control valve 86 in a conduit 88. A container or bottle sampler 90 is connected to conduits 22' and 82 by way of conduits 92 and 94, check valves 96 and 98, and a manual valve 100.

Switch assemblies 58' and 60' are operated as in FIG. 1 by a probe 102 connected to the outer end of a stem 104 which projects outwardly of the base end of cylinder 70 and which is connected to the one end of piston 72. Operation of piston 72 forwardly causes, when operated on-line, a sample of oil to be trapped in cylinder 80 which upon inward movement of piston 78 opens check valve 24' while holding closed check valves 96 and 98 and ejecting through particle counter 26' a predetermined volume of oil at a predetermined pressure as determined by the operation of switches 58' and 60', as previously explained, and by the operation of pressure compensated flow control valve 86. The latter valve is designed to permit a precise amount of oil to flow irrespective of variations of pressure existing upstream of the valve. Thus, valve 86 permits oil to flow through the by-pass sampling circuit so that the oil in cylinder 80 always is representative of the contamination level in the hydraulic system. Use of other types of flow control valves adjustable to deliver desired oil flow under high pressure conditions result in little or no flow through the valve when a particle count of a sample is not being taken, whereby sample oil is not necessarily representative of the oil condition of the system. Valves of the type illustrated schematically at 86 are manufactured by Fluid Controls of Mentor, Ohio.

Again, the particle counter is turned on and off and reset by switches 58' and 60' and, as will be appreciated, knob 102 may be adapted to also actuate switches for controlling air flow into conduits 74 or 76 for automatic cycling of the air cylinder.

As will be apparent, on the return stroke of piston 78 oil is drawn from conduit 14' by way of conduits 82, 94, 92 into cylinder 80 through open manual valve 84 and check valve 98. When the piston has completed its retraction oil is available to the cylinder by way of conduits 82 and 106. Shut-off valves 84 and 100 are used to shift the sampling operation between the on-line mode and the bottle sampling mode. In the on-line mode valve 84 is open and valve 100 is closed, whereas in the bottle sampling mode valve 84 will be closed and valve 100 open. When a bottle sample is desired line 108 is lowered into container 90 and piston 78 started from its extended position into cylinder 80. As the piston 78 is retracted by piston 72 through the application of air pressure into conduit 76 oil is drawn through the valves 100, 96 and conduits 108, 92 and 22' into cylinder 80 which, when the piston is fully retracted is full of oil. The piston is then actuated forwardly in cylinder 80 and the particle count of the bottle sample taken as described above relative to on-line sampling. It will be noted that cylinder 80 forms a part of the by-pass conduit means the same as in FIG. 1 and for the same advantageous purpose.

The embodiment of FIG. 2 is prefered to that of FIG. 1 primarily because of the availability of standardized and simpler parts to manufacture or procure, and because the use of pressure compensated valve 86 permits the use of the system with a variety of particle counters and with various flow rates, the required adjustment being merely to adjust the desired control pressure at the pressure compensator valve. In the FIG. 1 embodiment, on the other hand, such variations require a change in the linear rate of advance of the screw 44 and/or the speed of motor 46.

It will be apparent to those skilled in the art that various changes in the structure and relative arrangement of parts may be made without necessarily departing from the scope of my invention.

I claim:

1. Apparatus for counting particle contamination in a liquid comprising liquid conduit means which includes a liquid chamber, a piston adapted to operate in said chamber, spaced conduit opening means in said chamber, means for actuating said piston to cover one of said opening means subsequent to which actuation of said piston exhausts a measured volume of pressurized liquid from the other opening means, counting means connected to said conduit means for counting the particles in said measured volume of liquid, and valve means in said conduit means for establishing a predetermined liquid conduit pressure in said counting means when said piston actuating means is actuated.

2. Apparatus as claimed in claim 1 wherein said piston actuating means comprises motor means.

3. Apparatus as claimed in claim 2 wherein said motor means comprises a fluid actuated motor.

4. Apparatus as claimed in claim 3 wherein said fluid actuated motor is air operated.

5. Apparatus as claimed in claim 2 wherein said motor means comprises an electric motor, and means for converting rotational motor output to linear movement of said piston.

6. Apparatus as claimed in claim 1 wherein first and second switch means are operatively connected to said counting means and to said piston for operating said counting means between said first and second predetermined positions of said piston in said chamber.

7. Apparatus as claimed in claim 6 wherein said first switch means is operative to activate said counting means subsequent to closing said one opening means by said piston.

8. Apparatus as claimed in claim 1 wherein said liquid conduit means is connected to first and second spaced locations in a primary hydraulic system conduit such that liquid is adapted to flow through said conduit means, including said liquid chamber, from said first to said second location when said piston is retracted.

9. Apparatus as claimed in claim 8 wherein flow is restricted in said conduit means through said second location to said measured volume subsequent to closing of said one opening means by said piston.

10. Apparatus as claimed in claim 1 wherein said liquid conduit means is connected to first and second spaced locations in a primary hydraulic system conduit such that liquid is adapted to continuously flow through said conduit means, including said liquid chamber, from said first to said second location when said piston is retracted, whereby the liquid in said conduit means is representative of the contamination level in said hydraulic system conduit.

11. Apparatus as claimed in claims 1, 8 or 10 wherein said valve means comprises pressure compensated flow control valve means for maintaining a selected liquid back pressure in said liquid conduit means.

12. Apparatus as claimed in claim 11 wherein said valve means is adjustable to effect a constant back pressure in said counting means of at least substantially 1500 psi.

13. Apparatus as claimed in claim 1, 8 or 10 wherein said valve means comprises a two postion solenoid valve means and pressure relief valve means.

14. Apparatus as claimed in claim 13 wherein said valve means is adjustable to effect a constant back pressure in said counting means of at least substantially 1500 psi.

15. A method of counting particle contamination in a liquid of a hydraulic system comprising the steps of providing conduit means which includes an ejection chamber bypassing a portion of the hydraulic system, flowing liquid through the conduit means including the ejection chamber when the device is unengaged, providing a selectively engageable device in said ejection chamber for discharging a predetermined volume of liquid through a portion of the conduit means, maintaining a selected liquid back pressure in the conduit portion, and counting the particulate matter in the predetermined volume of liquid in the pressurized portion of the conduit means where the pressure at least so reduces the size of the air bubbles in the liquid that the counting is substantially of particulate matter only.

16. The method as claimed in claim 15 further comprising the step of maintaining the liquid back pressure at least at substantially 1500 psi.

17. Apparatus for counting particle contamination in a liquid comprising liquid conduit means which includes a liquid chamber, a piston adapted to operate in said chamber, spaced conduit opening means in said chamber, means for actuating said piston to cover one of said opening means subsequent to which actuation of said piston exhausts a measured volume of pressurized liquid from the other opening means, counting means connected to said conduit means for counting the particles in said measured volume of liquid, valve means in said conduit means for establishing a predetermined liquid conduit pressure in said counting means, and said conduit means including a conduit and check valve means by-passing said chamber for introducing liquid therein during retraction of said piston.

18. Apparatus as claimed in claim 17 wherein a container containing a liquid sample is adapted to be connected to said by-pass conduit, and valve means associated therewith for permitting said liquid sample to be drawn into said chamber for subsequent ejection by said piston through said counting means.

* * * * *